United States Patent
van den Bosch et al.

(10) Patent No.: US 8,748,701 B2
(45) Date of Patent: *Jun. 10, 2014

(54) INBRED BROCCOLI LINE BRM50-3905

(75) Inventors: Franciscus van den Bosch, Kesteren (NL); Meinardus Petrus Boon, Scharwoude (NL)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 61 days.

This patent is subject to a terminal disclaimer.

(21) Appl. No.: 13/336,401

(22) Filed: Dec. 23, 2011

(65) Prior Publication Data

US 2012/0096577 A1 Apr. 19, 2012

Related U.S. Application Data

(60) Continuation of application No. 12/893,701, filed on Sep. 29, 2010, now Pat. No. 8,101,827, which is a continuation of application No. 12/437,222, filed on May 7, 2009, now abandoned, which is a continuation of application No. 11/947,518, filed on Nov. 29, 2007, now Pat. No. 7,538,263, which is a continuation of application No. 10/640,719, filed on Aug. 13, 2003, now abandoned, which is a division of application No. 09/845,672, filed on Apr. 30, 2001, now Pat. No. 6,689,942.

(51) Int. Cl.
*A01H 5/00* (2006.01)
*A01H 5/10* (2006.01)
*A01H 1/00* (2006.01)
*C12N 15/82* (2006.01)

(52) U.S. Cl.
USPC .......................... 800/306; 800/260; 435/430

(58) Field of Classification Search
None
See application file for complete search history.

(56) References Cited

U.S. PATENT DOCUMENTS

| | | |
|---|---|---|
| 5,523,520 A | 6/1996 | Hunsperger |
| 5,945,582 A | 8/1999 | Sasayama et al. |
| 6,689,942 B2 | 2/2004 | van den Bosch et al. |
| 7,538,263 B2 * | 5/2009 | van der Bosch et al. ..... 800/306 |
| 8,101,827 B2 * | 1/2012 | van Den Bosch et al. .... 800/306 |

OTHER PUBLICATIONS

Ding et al, Annals of Botany 109: 747-759, 2012.*
Bennetzen et al., "Approaches and Progress in the Molecular Cloning of Plant Disease Resistance Genes," *Genetic Engineering*, vol. 14, pp. 99-124 (1992).
Cheung et al., "Conservation of S-locus for Self-incompatibility in *Brassica napus* (L.) and *Brassica oleracea* (L.)," *Theor. Appl. Genet.*, vol. 95, pp. 73-82 (1997).
Earle et al., "Cold-tolerant Ogura CMS *Brassica* Vegetables for Horticultural Use," *Cruciferae Newsletter*, vol. 16, pp. 80-81 (1994).
Eshed et al., "Less-Than-Additive Epistatic Interactions of Quantitative Trait Loci in Tomato," *Genetics*, vol. 143, pp. 1807-1817 (1996).
Kao et al., "Efficient plant regeneration from hypocotyl protoplasts of broccoli (*Brassica oleracea* L. ssp. *italica* Plenck)," *Plant Cell Reports*, vol. 9, pp. 311-315 (1990).
Kott et al., "The Role of Biotechnology in Canola/Rapeseed Research," *In* Rapeseed Production, Nutrition and Technology, Van Reinold, New York, pp. 47-78 (1990).
Kraft et al., "Linkage Disequilibrium and Fingerprinting in Sugar Beet," *Theor. Appl. Genet.*, vol. 101, pp. 323-326 (2000).
Pang et al., "Expression of a Gene Encoding a Scorpion Insectotoxin Peptide in Yeast, Bacteria, and Plants," *Gene*, vol. 116, pp. 165-172 (1992).

* cited by examiner

*Primary Examiner* — Elizabeth McElwain
(74) *Attorney, Agent, or Firm* — Alissa Eagle; Arnold & Porter LLP

(57) ABSTRACT

Inbred broccoli lines, designated BRM50-3906 are disclosed. The invention relates to the seeds of inbred broccoli lines BRM50-3906, to the plants of inbred broccoli lines BRM50-3906, and to methods for producing a broccoli plant produced by crossing the inbred line BRM50-3906 with itself or another broccoli line. The invention further relates to hybrid broccoli seeds and plants produced by crossing the inbred line BRM50-3906 with another broccoli line.

8 Claims, No Drawings

INBRED BROCCOLI LINE BRM50-3905

CROSS-REFERENCE TO RELATED APPLICATIONS

This application is a continuation of U.S. patent application Ser. No. 12/893,701, filed Sep. 29, 2010 (now U.S. Pat. No. 8,101,827, issued Jan. 24, 2012), which is a continuation of U.S. patent application Ser. No. 12/437,222, filed May 7, 2009 (abandoned), which is a continuation of U.S. patent application Ser. No. 11/947,518, filed Nov. 29, 2007 (now U.S. Pat. No. 7,538,263, issued May 26, 2009), which is a continuation of U.S. patent application Ser. No. 10/640,719, filed Aug. 13, 2003 (abandoned), which is a divisional of U.S. patent application Ser. No. 09/845,672, filed Apr. 30, 2001 (now U.S. Pat. No. 6,689,942, issued Feb. 10, 2004), all of which applications and patents are herein incorporated by reference in their entireties.

BACKGROUND OF THE INVENTION

This invention relates to new and distinctive broccoli inbred line, designated BRM50-3906. There are numerous steps involved in the development of any new and novel desirable germplasm with superior combining ability. Plant breeding begins with the analysis and definition of problems and weaknesses of the current germplasm, the establishment of program goals, and definition of specific breeding objectives. The next step is selection of germplasm that posses the traits to meet the program goals and the best breeding method to reach those goals. The objective is to combine in a single variety or hybrid an improved combination of desirable traits from the parental germplasm. These important characteristics may include higher yield, better flavor, improved color and field holding ability, resistance to diseases and insects along with economic seed yields to facilitate the cost of hybrid seed production.

The method chosen for breeding or selection depends on the mode of plant reproduction, the heritability of the trait(s) being improved, and the cultivar (variety) used commercially (e.g. $F_1$ hybrid, pureline). The complexity of inheritance influences choice of breeding method. A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, observation in multiple locations and seasons provide a better estimate of its genetic worth.

The development of commercial broccoli hybrids requires the development of homozygous inbred lines. Breeding programs combine desirable traits from two or more germplasm sources from which various broad based breeding gene pools are used to develop inbred lines by selfing followed by selection of desired phenotypes sometimes utilizing anther, microspore and ovule culture to speed up and improve selection efficiency.

The goal of plant breeding is to develop new, unique, and superior broccoli cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same broccoli traits.

Description of breeding methods that are commonly used for different traits and crops can be found in one of several reference books (e.g. Allard, R.W. "Principles of Plant Breeding" John Wiley and Son, pp.115-161, 1960; Simmonds, 1979; Sneep et al., 1979; Fehr, 1987).

Proper testing and evaluation should detect any major faults and establish the level of superiority or improvement over current cultivars. In addition to showing superior performance, there must be a demand for a new cultivar that is compatible with industry standards or which creates a new market. For seed-propagated cultivars, it must be feasible to maintain the inbred lines and produce seed easily and economically.

Broccoli, *Brassica oleracea* L., is a new crop in North, South and Central America, Europe and Asia. The introduction of hybrid cultivars in the 1960's provided a magnitude increase in yield, holding ability, expanded growing seasons and large scale production of broccoli. The goal in broccoli breeding is to make continued improvement in hybrid broccoli yields and horticultural characteristics in order to sustain the supply to meet continuous increase in demand for broccoli in developed and emerging world economies. To accomplish this goal new breeding methods such as anther culture and microspore culture have been utilized to more rapidly generate inbred broccoli lines from more diverse germplasm sources.

Broccoli (*Brassica oleracea*, L.) belongs to the mustard family. All *Brassica oleracea* will cross pollinate. Pollination is effected by insect vectors, most common of which is the honey bee. Broccoli, like most other *Brassica*, have a genetic characteristic of self incompatibility which encourages cross pollination resulting in higher levels of variability. Variability in populations is desired for wide adaptation and survival. Broccoli breeding populations can be inbred or backcrossed for 8 to 9 generations and/or with the use of double haploids derived from anther culture to develop homozygous inbred lines. Broccoli $F_1$ hybrids can be produced by using self-incompatibility or cytoplasmic male sterility to control pollen movement between selected inbred lines.

Self-incompatibility is a breeding system that enforces outcrossing and therefore maximizes recombination in cross pollinated species. This breeding system in nature has been utilized by man in $F_1$ hybrid breeding, especially in *Brassica* vegetables (Tsunoda et al., chapter 13).

Cytoplasmic male sterility (CMS) is another method used in *Brassica* vegetables species to produce $F_1$ hybrids. This method of producing hybrids in *Brassica* is a more recent development compared to self-incompatibility. A genetic mutation contained in the cytoplasm (mitochondria) is responsible for the lack of production of pollen. In *Brassica*, the cytoplasm has commonly been identified in and transferred from "Ogura"-type radish (Ogura, 1968). The major advantage of CMS over self-incompatibility is that under normal conditions, no pollen is produced in the female parent. This results in the production of 100% hybrid seed. Under certain stressful growth conditions, however, it may be possible to produce small amounts of fertile pollen in CMS plants. *Brassica* inbreds containing CMS are maintained by continued hybridization to their normal (fertile) counterpart inbred, commonly referred to as a "B" line.

The plants associated with the *Brassica* group have been familiar to mankind since ancient times, and always of great agricultural importance. *Brassica* is a major food species worldwide. *Brassica* species have a general adaptation for cool climate growing conditions. Therefore, adaptation has occurred for summer growing conditions with cool to moderate climates and for winter growing conditions in warmer or tropical locations.

SUMMARY OF THE INVENTION

The invention comprises a novel inbred broccoli line, designated BRM50-3906. This invention thus relates to the seeds of inbred broccoli line BRM50-3906, to the plants of inbred broccoli line BRM50-3906, to methods used for controlling pollination when making hybrid seed with BRM50-3906, and to methods for producing a broccoli plant by crossing the inbred broccoli line BRM50-3906 with itself or another broccoli line. This invention further relates to hybrid broccoli seeds and plants produced by crossing the inbred line BRM50-3906 with another broccoli line.

DETAILED DESCRIPTION OF THE NEW PLANT

Definitions

In the description and tables which follow, a number of terms are used. In order to provide a clear and consistent understanding of the specification and claims, including the scope to be given such terms, the following definitions are provided.

Average Weight: The average weight is the average weight for an entire plot of harvested broccoli head.

Overall Rating Score: This Overall Rating Score is rated on a scale of 1 to 5. A score of 5 indicated an excellent overall rating. A score of 3.0 indicates average, and a score of 1 indicates poor.

Color: Color means the color of the head at maturity.

Disease and Insect Ratings: Disease and Insects are rated on a scale of 1 to 5. A score of 5 indicates severe damage. A score of 3.0 indicates moderate damage, and a score of 1 indicates no damage.

Inbred broccoli (*Brassica oleracea* L.) BRM50-3906 has superior characteristics, and provide an excellent parental line in crosses for producing first generation ($F_1$) hybrid broccoli. The $F_1$ hybrids with BRM50-3906 have a high tolerance to bacterial soft rot which is very important in areas with high rainfall and humidity like northwestern Europe and which results in higher returns to the grower and improved shelf life. The $F_1$ hybrids with BRM50-3906 have a high tolerance to hollow stem which is important in areas with lower planting densities and/or fast growth which results in improved shelf life and higher returns to the grower. The $F_1$ hybrids with BRM50-3906 have a high tolerance to 'cateyes' which result in a more attractive product with uniform bead. The $F_1$ hybrids of the instant invention produce a more compact and solid head which result in higher weight per head and head diameter as compared to commercial hybrids, Marathon, Legacy and Decathlon which in turn increases yield for the grower and provides a better product for processing since the outer florets do not crumble. BRM50-3906 produce a more 'open' plant type, narrower leaf petioles and smaller scars on the stem which makes the product easier to harvest and clean, decreasing labor costs and increasing returns to the grower. The longer field standing ability of BRM50-3906 provides greater flexibility to the grower. With the combination of all of these improved traits, the yield is increased over the leading commercial broccoli varieties Marathon, Legacy and Decathlon.

The inbred has shown uniformity and stability for all traits, as described in the following variety description information. The line has been increased and maintained by pollination with fertile inbred line GIX with continued observation for uniformity.

Variety Description Information

A cytoplasmic male sterility gene was backcrossed into BRM50-3905 to produce BMR50-3906. BMR50-3906 is maintained by cross pollination with a fertile maintainer line which is maintained by self-pollination. BMR50-3906 has the following characteristics:

Maturity: Late
Plant Characteristics:
No. of Stems: 1
Head Color: Blue-green
Plant Height: Tall This invention is also directed to methods for producing a broccoli by crossing a first parent broccoli plant with a second parent broccoli plant, wherein the first or second broccoli plant is the inbred broccoli from the line BMR50-3906. Further, both first and second parent broccoli plants may be from the inbred line BMR50-3906. Therefore, any methods using the inbred broccoli line BMR50-3906 are part of this invention; selfing, backcrosses, hybrid breeding, and crosses to populations. Any plants produced using inbred broccoli line BMR50-3906 as a parent are within the scope of this invention. Advantageously, the inbred broccoli line is used in crosses with other broccoli varieties to produce first generation ($F_1$) broccoli hybrid seed and plants with superior characteristics.

As used herein, the term "plant" includes plant cells, plant protoplasts, plant cells of tissue culture from which broccoli plants can be regenerated, plant calli, plant dumps, and plant cells that are intact in plants or parts of plants, such as pollen, flowers, seeds, stalks, stumps, leaves and the like. Thus, another aspect of this invention is to provide for cells which upon growth and differentiation produce the inbred broccoli BMR50-3906.

Table

In Table 1 that follows, the traits and characteristics of the hybrid RS 1140 which has BRM50-3905 as one of its parents, are given in comparison with other commercial broccoli varieties.

As shown in the Table, RS1140 which is the variety which has BRM50-3905 as one of its parents clearly outperforms the other commercial varieties, Marathon, Decathlon and Legacy in most categories.

| Name | 50% Mat. | Avg Wt | Unif | Plant Type | Head Type | Bead Size | Stem Quality | Overall | Disease |
|---|---|---|---|---|---|---|---|---|---|
| Broccoli Trait Comparison United Kingdom - 1999 Plant Date: July 20 | | | | | | | | | |
| RS1140 | Oct 15 | 500 | 4.5 | 4.5 | 4.5 | 4.5 | 4.5 | 4.5 | 4.0 |
| Marathon | Oct 13 | 480 | 2.0 | 4.0 | 3.0 | 4.0 | 3.0 | 3.0 | 4.0 |
| Decathlon | Oct 6 | 350 | 3.5 | 4.5 | 3.0 | 4.0 | 4.0 | 3.0 | 4.5 |

-continued

| Name | 50% Mat. | Avg Wt | Unif | Plant Type | Head Type | Bead Size | Stem Quality | Overall | Disease |
|---|---|---|---|---|---|---|---|---|---|
| | | | | Broccoli Trait Comparison United Kingdom - 2000 Plant Date: July 5 | | | | | |
| RS1140 | Sep 19 | 670* | 3.0 | 5.0 | 5.0 | 3.5 | 4.5 | 4.5 | 3.5 |
| Marathon | Sep 13 | 600 | 3.0 | 3.0 | 2.5 | 4.0 | — | 2.5 | 3.5 |
| Legacy | Sep 13 | 620 | 2.5 | 3.5 | 3.0 | 4.0 | — | 3.0 | 3.5 |

*Due to an unusually poor seed lot this number has been recalculated.

Deposit Information

Deposit of the *Brassica* seeds BRM50-3906 of this invention are maintained by Seminis Vegetable Seeds, 37437 State Highway 16, Woodland, Calif. 95695. Access to these deposits will be available during the pendency of this application to persons determined by the Commissioner of Patents and Trademarks to be entitled thereto under 37 CFR 1.14 and 35 USC 122. Upon allowance of claims in this application, all restrictions on the availability to the public of the variety will be irrevocably removed by affording access to a deposit of at least 2,500 seeds of the same variety with the American Type Culture Collection, Manassas, Va. A deposit of the Seminis Vegetable Seeds proprietary inbred broccoli line BRM50-3905 has been made with the American Type Culture Collection (ATCC), 10801 University Boulevard, Manassas, Va. 20110. The date of deposit was May 15, 2003. The ATCC Accession Number is PTA-5198.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method of breeding a broccoli plant comprising:
   a. selecting a first parent broccoli plant, wherein said first parent broccoli plant is a plant of broccoli line BRM50-3905, a sample of seed of said line having been deposited with the American Type Culture Collection under ATCC Accession No. PTA-5198, and selecting a second parent broccoli plant having a characteristic selected from the group consisting of resistance to bacterial disease, resistance to fungal disease, resistance to viral disease, resistance to insects, and resistance to herbicide;
   b. crossing said first parent broccoli plant with said second parent broccoli plant to obtain progeny plant seed;
   c. growing said progeny plant seed into a third broccoli plant and selecting said third broccoli plant for said characteristic; and
   d. performing one or more backcrosses and selection for said characteristic to said first parent broccoli plant to develop a homozygous inbred broccoli plant line having said characteristic.

2. The method of claim 1, wherein said homozygous inbred broccoli plant line comprises a single gene conversion.

3. The method of claim 2, wherein said single gene conversion comprises said characteristic.

4. The method of claim 1, wherein said characteristic is resistance to bacterial disease.

5. The method of claim 1, wherein said characteristic is resistance to fungal disease.

6. The method of claim 1, wherein said characteristic is resistance to viral disease.

7. The method of claim 1, wherein said characteristic is resistance to herbicide.

8. The method of claim 1, wherein said characteristic is resistance to insects.

* * * * *